(12) United States Patent
Colfer

(10) Patent No.: US 7,279,614 B2
(45) Date of Patent: Oct. 9, 2007

(54) ARTICHOKE HYBRID NAMED 'PS-H1855'

(75) Inventor: William J. Colfer, Aptos, CA (US)

(73) Assignees: Plant Sciences, Inc., Watsonville, CA (US); Ocean Mist Farms, Castroville, CA (US)

( * ) Notice: Subject to any disclaimer, the term of this patent is extended or adjusted under 35 U.S.C. 154(b) by 380 days.

(21) Appl. No.: 11/079,406

(22) Filed: Mar. 15, 2005

(65) Prior Publication Data

US 2006/0272043 A1    Nov. 30, 2006

(51) Int. Cl.
*A01H 5/00* (2006.01)
*A01H 5/10* (2006.01)
*A01H 1/02* (2006.01)

(52) U.S. Cl. .................. 800/260; 800/295; 800/298
(58) Field of Classification Search .................. None
See application file for complete search history.

*Primary Examiner*—Phuong Bui
*Assistant Examiner*—Brent T Page
(74) *Attorney, Agent, or Firm*—Foley & Lardner LLP

(57) ABSTRACT

A new and distinct artichoke hybrid named 'PS-H1855', characterized by its numerous bud numbers, fleshiness of bracts, fleshiness of hearts, uniformity of head shapes and ability to bolt in warm summer conditions (reduced vernalization requirements) allowing spring/summer planting and fall production.

7 Claims, 4 Drawing Sheets
(4 of 4 Drawing Sheet(s) Filed in Color)

ARTICHOKE HYBRID NAMED 'PS-H1855'

FIELD OF INVENTION

The present invention relates to an artichoke hybrid designated 'PS-H1855', as well as, heads produced by this hybrid.

BACKGROUND OF THE INVENTION

The present invention comprises a new and distinct artichoke hybrid, botanically known as *Cynara scolymus* L. and herein referred to by the varietal designation 'PS-H1855'.

*Cynara scolymus* L., commonly known as Globe artichoke, is a thistle-like perennial and is a member of the family *Asteraceae*. Globe artichokes comprise leaves which are pinnately lobed with primarily a spiney and oval capitula composed of an involucre made up of overlapping layers of large bracts and a receptacle which are enlarged and fleshy. Globe artichoke plants may be propagated by division and are essentially grown for the production of the immature flower heads that are vegetable delicacies. Fresh artichokes may be steamed or boiled, after which the fleshy receptacle, inner and outer bracts, and parts of the floral stem may be eaten.

SUMMARY OF THE INVENTION

The new hybrid is a product of a planned breeding program conducted in Chowchilla, Calif. in 2002. The new hybrid is produced by crossing two proprietary *Cynara scolymus* L. lines; the female parent designated as 'PS-msG0801' and the male parent designated as 'RCHB01'.

An objective of the present invention is to provide seeds to produce artichoke hybrid 'PS-H1855'. Another objective of the present invention is to provide heads produced by the artichoke hybrid 'PS-H1855'.

The new hybrid has not been observed under all possible environmental conditions. The phenotype may vary with variations in environment such as temperature, light intensity and day length, without any change in the genotype of the hybrid.

BRIEF DESCRIPTION OF THE DRAWING

The patent or application file contains at least one drawing executed in color. Copies of this patent or patent application publication with color drawings will be provided by the Office upon request and payment of the necessary fees.

DETAILED DESCRIPTION

Figure 1:
FIG. 1. The first photograph shows many 'PS-H1855' plants grown in the field.
Figure 2:
FIG. 2. The second photograph shows a close-up of an artichoke of a 'PS-H1855' plant grown in the field.
Figure 3:
FIG. 3. The third photograph shows a close-up of the head of an artichoke of a 'PS-H1855' plant grown in the field.
Figure 4:
FIG. 4. The fourth photograph shows a filled carton of variable head sizes of 'PS-H1855' artichokes.

The following observations, measurements and values describe plants of 'PS-H1855' grown in Castroville, Calif., under conditions which closely approximate those generally used in horticultural practice.

'PS-H1855' seeds were deposited at the American Type Culture Collection (ATCC), P.O. Box 1549, Manassas, Va. 20108, U.S.A., and accorded ATCC accession no. PTA-6540.

All color references below are measured against The Munsell Book of Color, Munsell Color Macbeth Division of Kollmorgen Instruments Corporation. Colors are approximate as color depends on horticultural practices such as light level and fertilization rate, among others.

Castroville is located in California's central coast. Conditions can vary greatly during the summer months. Air temperature can range between about 20° F. in the winter to above 80° F. during the summer months. Relative humidity is generally moderate with values ranging from the mid 40's to the high 60's. Prevailing winds are westerly and rainfall rarely exceeds 25' inches.

In the following description, holding quality was measured by the physical appearance of the harvested heads. This includes the heads appearance following 3, 7 and 10 day storage periods in a cold storage room held at 34° F. Head exterior (oxidation) was observed at each of the three observation points. Browning and blackening of plant tissue was evaluated as light, moderate and extreme. Juiciness was measured by observing exudate and rated as absent, moderate or excessive. Overall storage response was measured by observations concentrated on visible color variability and/or presence of lesions or other cosmetic anomalies. Leaf ratio (L/W) was determined by dividing representative leaf sample length measurements by representative leaf sample width measurements. Finally, head response to weather was determined by observing the heads at maturity. These field observations focus on the presence or absence of bronzing, necrotic and chlorotic lesions or any abiotic response to environmental conditions, where possible plant phenotypes are correlated with environmental conditions.

It should be noted that these data were collected from first year transplants. These data are subject to change depending upon time of planting and environmental conditions. The new and distinct cultivar of artichoke plant named 'PS-H1855' is characterized by:

1. numerous bud numbers;
2. fleshiness of bracts;
3. fleshiness of hearts;
4. uniformity of head shapes; and
5. ability to bolt in warm summer conditions (reduced vernalization requirements) allowing spring/summer planting and fall production.

Parentage:
Male parent: Proprietary *Cynara scolymus* L. line designated 'RCHB01'
Female parent: Proprietary *Cynara scolymus* L. line designated 'PS-msG0801'
Classification: Botanical: *Cynara scolymus* L. Commercial: artichoke c.v. PS-H1855
Propagation: Seed production
Plant:
Height: About 123.80 cm Range: 114.33-132.74 cm
Width: About 215.39 cm Range: 166.10-202.56 cm
Growth Habit: Upright/intermediate
Side Shoots: About 3.86 Range: 2.0-6.0
Foliage Density: Open to moderate, variable shoots give plant a open to moderate plant density appearance.
Side Shoot Development: Moderate side shoot development.
Capitulum:
Size: (12)Primary: 36.20-38.10 cm (18) Secondary: 28.58-30.40 cm (24) Secondary: 31.12-33.02 cm (30) Tertiarty: 28.58-30.48 cm (36) Tertiarty: 26.04-27.94 cm (48) Tertiarty: 23.50-25.40 cm
Shape: Oval. Oval shape can have increased mid-section dimensions.

Number: About 6.67 heads/plant Range: 5.0-8.0 heads/plant
Texture: Intermediate, smooth.
Fragrance: Mild, lightly aromatic.
Bract Size: About 9.33 cm (l)×6.23 cm (w) Range: 7.6-9.6 cm (l)×5.4-6.6 cm (w)
Bract Shape: Bracts are predominantly oval shaped with constricted (narrow) basal regions on inner bracts.
Bract Texture: Smooth, slight texture.
Bract Number: About 54.40 bracts Range: 50-62 bracts
Bract Color: Inner: 10 Y 9/1-10 Y 9/2 (White coloration) Inner: 5 GY 6/4-5 GY 6/6 (Green Coloration) Outer: 5 GY 6/6-5 GY 6/4-5 GY 4/4 (Green Coloration) Outer: 10 RP 4/6-10 RP 3/6-10 RP 3/4-5 RP 2/4 (Blush Coloration)
Bract Basal Thickness: About 7.48 mm Range: 6.0-9.0 mm
Heart Description: Concave, full. Heart is nearly flat, very little concave quality.
Heart Color: 10Y 9/2
Papus Length: About 19.20 mm Range: 17.0-22.0 mm
Papus Color: Variable white coloration.
Overall Cold Storage Good cold storage response. Observations made on day 3, 7 and 10 was good, displaying only light oxidation (light
Response: browning).
Head Firmness: Heads are moderately firm.
Bract Firmness: Moderate. Bracts are brittle with reduced malleability.
Gloss: Dull. Heads have very little glossiness.
Cold Storage (hold Good. Only a slight "browning" was observed on some bract quality): edges.
Head Exterior Moderate. Only those areas damaged during harvest showed (oxidation): some oxidation.
Juiciness: Absent. Peduncle and bract exudate is slight.
Head Response to No adverse plant responses were observed, to any of the weather: weather conditions which included direct sunlight (warm and sunny) and diffused sunlight (foggy, cool) field conditions.
Foliage:
Length: About 127.33 cm Range: 119.6-138.7 cm
Width: About 84.38 cm Range: 77.22-91.69 cm
Leaf Serrations: About 57.33 mm Range: 42.0-82.0 mm
Leaf Basal Angle: About 32.92 degrees Range: 25.0-42.0 degrees
Leaf Ratio (L/W): About 1.50 Range: 1.35-1.80
Leaf Area: About 10,679.50 cm$^2$ Range: 10,474.82-11,434.17 cm$^2$
Color: 5 GY 4/2-5 GY 4/6
Texture: Slightly textured. Immature developing leaves are smooth.
Older leaves slightly blistered surface.
Venation: Prominent, greenish/white. Both mid-vein and surrounding venation are light green colored.
Pubescence: Smooth to sparse density. Pubescence on most leaves is indistinct.
Leaf Basal Thickness: About 11.40 mm Range: 10.67-11.67 mm
Leaf Distance Between About 56.70 mm Serrations: Range: 45.1-60.7 mm
Petiole Length: About 10.14 cm Range: 9.43-10.4 cm
Petiole Width: About 37.10 mm Range: 33.0-40.0 mm
DISEASE No observations made. RESISTANCE:

Artichoke hybrid 'PS-H1855' produces plants with a moderate height, ranging from 114-132 cm. In comparison to artichoke variety 'Green Globe', 'PS-H1855' has a similar green (non-glossy) exterior coloration, but a greater number of heads per plant. Head numbers are about 4-8 per 'PS-H1855' plant. Head shape is predominately oval. The non-glossy heads are produced in sizes ranging from size (12) primary, sizes (18 and 24) secondary, and sizes (30, 36 and 48) tertiary.[1] Anthocyanin coloration is present on the innermost interior bracts and found on only some outer, exterior bract edges. Its presence is characterized as light and is usually confined to the basal portions of the head. The head spinosity is slightly more prominent on bract apexes that are acute as well as those bracts that are slightly notched. The average spine length ranges between 1.8-3.0 mm. The plants upright growth habit is intermediate, but is very vigorous. The canopy coloration is a deeper green/green/yellow color with some colors ranging towards darker green/green/grey hues. These colors on Munsell Leaf Color Chart range from 5 GY 4/2-5 GY 4/6. Leaf spinosity is light to moderate, categorized as few. Floral stalk development during anthesis produces a purple flower. Flower color changes as the flower matures. The phenotypic characteristics of this cultivar may vary slightly, depending upon variation in the environmental factors, including weather (temperature, humidity and light intensity), day length, soil type, farming practices, location and time of year.

[1] These numbers reflect the number of artichoke heads required to fill a standard artichoke carton. For example, the small 36 size requires 36 artichokes of that size to fill the carton.

I claim:

1. Seeds that produce artichoke plants designated 'PS-H1855' and having American Type Culture Collection Deposit Accession No. PTA-6540.

2. The artichoke plants designated 'PS-H1855' produced from seeds accorded American Type Culture Collection Deposit Accession No. PTA-6540.

3. Pollen produced by the plants of claim 2.

4. Seeds produced by the plants of claim 2.

5. Heads produced by the plants of claim 2.

6. A method of producing a new artichoke plant comprising crossing 'PS-H1855', either as the male or female parent, with a second artichoke plant, and selecting progeny.

7. The method according to claim 6, wherein the second artichoke plant is 'PS-H1855'.

* * * * *